(12) United States Patent
Henrikson

(10) Patent No.: US 8,419,324 B2
(45) Date of Patent: Apr. 16, 2013

(54) METHOD AND DEVICE FOR CONTROLLING A TOOL WITH ULTRASONIC WAVES

(75) Inventor: Per Henrikson, Trollhättan (SE)

(73) Assignee: Volvo Aero Corporation, Trollhättan (SE)

( * ) Notice: Subject to any disclaimer, the term of this patent is extended or adjusted under 35 U.S.C. 154(b) by 1367 days.

(21) Appl. No.: 12/089,185

(22) PCT Filed: Oct. 21, 2005

(86) PCT No.: PCT/SE2005/001588
§ 371 (c)(1),
(2), (4) Date: Apr. 3, 2008

(87) PCT Pub. No.: WO2007/046737
PCT Pub. Date: Apr. 26, 2007

(65) Prior Publication Data
US 2008/0260482 A1   Oct. 23, 2008

(51) Int. Cl.
*B23Q 17/20* (2006.01)
(52) U.S. Cl.
USPC ............ 409/133; 409/132; 409/195; 409/207
(58) Field of Classification Search ............... 409/131, 409/132, 133, 135, 136, 143, 186, 187, 188, 409/193, 194, 195, 207, 208, 209; 73/632, 73/633, 634, 641
See application file for complete search history.

(56) References Cited

U.S. PATENT DOCUMENTS

| | | | |
|---|---|---|---|
| 3,483,795 A * | 12/1969 | Wranosky | 409/80 |
| 3,834,256 A * | 9/1974 | Abbatiello et al. | 82/133 |
| 3,935,766 A * | 2/1976 | Masters | 82/133 |
| 4,026,143 A * | 5/1977 | Holland | 73/596 |
| 4,362,059 A * | 12/1982 | Zwyssig | 73/628 |
| 4,489,611 A * | 12/1984 | Zimmermann et al. | 73/625 |
| 4,620,281 A | 10/1986 | Thompson et al. | |
| 4,786,219 A * | 11/1988 | Oberlin et al. | 409/84 |
| 4,787,136 A | 11/1988 | Majic | |
| 5,361,470 A * | 11/1994 | Hamada et al. | 29/27 R |
| 5,747,693 A * | 5/1998 | Abbate et al. | 73/622 |
| 5,850,184 A * | 12/1998 | Bailey et al. | 340/680 |
| 5,948,985 A * | 9/1999 | Brautigan et al. | 73/622 |

FOREIGN PATENT DOCUMENTS

| | | |
|---|---|---|
| EP | 0321108 A2 | 6/1989 |
| FR | 2287679 A1 | 5/1976 |
| JP | 6055414 A1 | 3/1994 |

OTHER PUBLICATIONS

International Search Report from corresponding International Application No. PCT/SE2005/001588, Jun. 13, 2006.

* cited by examiner

*Primary Examiner* — Edward Tolan
(74) *Attorney, Agent, or Firm* — WRB-IP LLP

(57) ABSTRACT

In a method for controlling a tool during machining a work piece using the tool, a first measuring arrangement which has a first ultrasonic probe for emitting ultrasonic waves is used, the first measuring arrangement being arranged ahead of the tool with respect to the relative tool movement direction and being moved relative to the work piece in the relative tool movement direction. The ultrasonic waves emitted by the first ultrasonic probe are transmitted to the work piece, and are transmitted back to the first ultrasonic probe, by a first column of liquid which is created by the first measuring arrangement and situated between the first ultrasonic probe and the work piece for measurement. The measurements are used for automatically adjusting the position of the tool relative to the work piece during machining the work piece.

28 Claims, 2 Drawing Sheets

METHOD AND DEVICE FOR CONTROLLING A TOOL WITH ULTRASONIC WAVES

BACKGROUND AND SUMMARY

The present invention relates to a method for controlling a tool during machining a work piece by means of the tool.

The invention is applicable to different combinations of cutting tools and work pieces. For example, during a turning or milling operation, the tool can be controlled so as to obtain the requisite dimensions of the machined work piece. Particularly, the invention can be used during milling narrow grooves in a thin structure, such as a sheet, where the resulted wall thickness of the thin structure is critical to the performance of the final product. Such sheets are frequently used for production of combustion chambers, such as rocket nozzles which are provided with long narrow cooling channels.

In the manufacturing industry where metal work pieces are subjected to different machining operations, such as milling and turning, there are often tolerance requirements on the component resulted from the work piece, which requirements are based on for example stipulated maximum and minimum values for the dimensions of the final product.

After the machining operation, some kind of verification process has to be accomplished to secure the tolerance requirements on the component being fulfilled. Normally, the verification process is performed on the component after the machining operation has been finished, and thus the verification process and the machining process are two separate processes. This means that if the machining operation has not been successful resulting in a defective component, the component may have to be machined again or even be rejected.

For example the milling operation using a side-milling cutter to form very long narrow grooves in sheets intended for combustion chambers is a very time consuming and complex process resulting in expensive components. Particularly, conical components such as rocket nozzles having curved surfaces are very difficult to machine. Furthermore, there are very rigorous tolerance requirements on such a component which makes greats demands on accuracy of the milling process and equipments, such as tool, fixture etc., and on the verification process as well. In addition, it is not possible for practical reasons to check the wall thickness resulted from the milling operation in every single point along the bottom of the milled grooves. Another problem arises from the fact that these particular types of component often have machined grooves with a cross section size down to approximately 1×2 mm, which implies the instruments for measuring the thickness of the material must have very small dimensions to be applied in the grooves.

According to prior art ultrasonic technique is used for some types of verification of components, such as investigation of any material defects inside the material and for determination of the wall thickness of a component. The crystal of the ultrasonic probe is brought into mechanical contact with the surface of the component and the propagation of ultrasonic waves between the probe and the component is facilitated by applying a transmission medium, such as a gel on the component. Ultrasonic waves reflected from the component can give information about the interior structure of the material and the wall thickness as well. However, to achieve a useful result it is important to arrange the crystal in a certain angle relative to the surface of the component, and establish a certain contact pressure between the probe and the component. Furthermore, the gel has to be evenly distributed on the surface of the component where the probe contacts the surface of the component. Accordingly, measurements can only be performed on certain discrete points of the component and an operator has to carry out all the steps involved when moving the probe to a new measurement point over again for each point to be measured.

In another type of investigation by means of ultrasonic waves the whole component to be inspected is immersed in water used for the propagation of the ultrasonic waves. Usually, due to practical reasons this method cannot be used for large or immoveable components.

A further type of verification process is based on mechanical contact between a measuring probe, such as a metal sphere, and the component to be measured. Measurements of the variation of a magnetic field created between the probe and a second metal component arranged at the opposite side of the component give information about the wall thickness of the component.

It is desirable to provide a method of the type mentioned by way of introduction, the method enabling better control of the cutting depth or the final wall thickness, and, thus enabling a machined component to be produced with greater accuracy.

According to an aspect of the invention, a first measuring arrangement has a first ultrasonic probe for emitting ultrasonic waves, the first measuring arrangement being arranged ahead of the tool with respect to the relative tool movement direction and being moved relative to the work piece in the relative tool movement direction, wherein ultrasonic waves emitted by the first ultrasonic probe are transmitted to the work piece, and are transmitted back to the first ultrasonic probe, by means of a first column of liquid which is created by the first measuring arrangement and situated between the first ultrasonic probe and the work piece for measurement, and using the measurement for automatically adjusting the position of the tool relative to the work piece during machining the work piece.

According to an aspect of the invention, the method comprises the step of transmitting the ultrasonic waves emitted by the first ultrasonic probe to a first surface of the work piece, that the first column of liquid is situated between the first ultrasonic probe and the first surface, for measuring the distance from the first ultrasonic probe to the first surface, and using the distance measurements for automatically adjusting the position of the tool relative to the work piece during machining the work piece.

By such a method the position of the tool relative to the work piece, and, thus at least a theoretical cutting depth can continuously be calculated and the tool can be adjusted in accordance therewith. In case the conditions can be approximated to be constant, i.e. negligible tool wear etc., the calculated cutting depth is the real cutting depth.

According to a preferred embodiment of the invention, the method comprises the step of using the first ultrasonic probe for measuring the thickness of the work piece between the first surface and a second surface of the work piece, and using the thickness measurements for automatically adjusting the position of the tool relative to the work piece during machining the work piece. By such a method the process can be controlled so as to obtain a desired wall thickness of the work piece after being machined, without any prior information about the original thickness of the work piece.

According to another preferred embodiment of the invention a second measuring arrangement having a second ultrasonic probe for emitting ultrasonic waves is used, the second measuring arrangement being arranged after the tool with respect to the relative tool movement direction and being moved relative to the work piece in the relative tool movement direction, wherein ultrasonic waves emitted by the second ultrasonic probe are transmitted to a surface of the work piece which surface has been machined by the tool, and are transmitted back to the second ultrasonic probe, by means of a second column of liquid which is created by the second measuring arrangement and situated between the second ultrasonic probe and the machined surface, and the measurements accomplished by the second ultrasonic probe are used for automatically adjusting the position of the tool relative to the work piece during machining the work piece.

The second ultrasonic probe can also be used for measuring the distance between the machined surface and a second surface of the work piece, i.e. the thickness of the work piece. Alternatively, the thickness can be calculated by using the distance to the machined surface and information about the original thickness in the current position or information about the distance to the second surface obtained for example by means of the first ultrasonic probe.

By such a method the verification process can be accomplished during the machining operation and the tool can be adjusted during machining so as to compensate for tool wear and/or variation of the material characteristics or dimensions of the work piece. The verification process can be continuously accomplished and measurements can be performed at several positions along the work piece. The tool, for example a side-milling cutter blade, usually comprises one or more hard metal inserts. The performance of the tool is very much dependent on the degree of wear of these inserts. Hence it is desirable to continuously compensate for wear of the inserts so as to ensure the cutting operation will give the desired result. For this purpose the tool and the work piece can be brought towards each other based on the measurements accomplished by the ultrasonic probes.

Other advantageous features and functions of different embodiments of the invention appear from the following detailed description.

BRIEF DESCRIPTION OF THE DRAWINGS

With reference to the appended drawings, below follows a more detailed description of preferred embodiments of the invention provided merely as non-limiting examples.

DETAILED DESCRIPTION

Figure 1A:
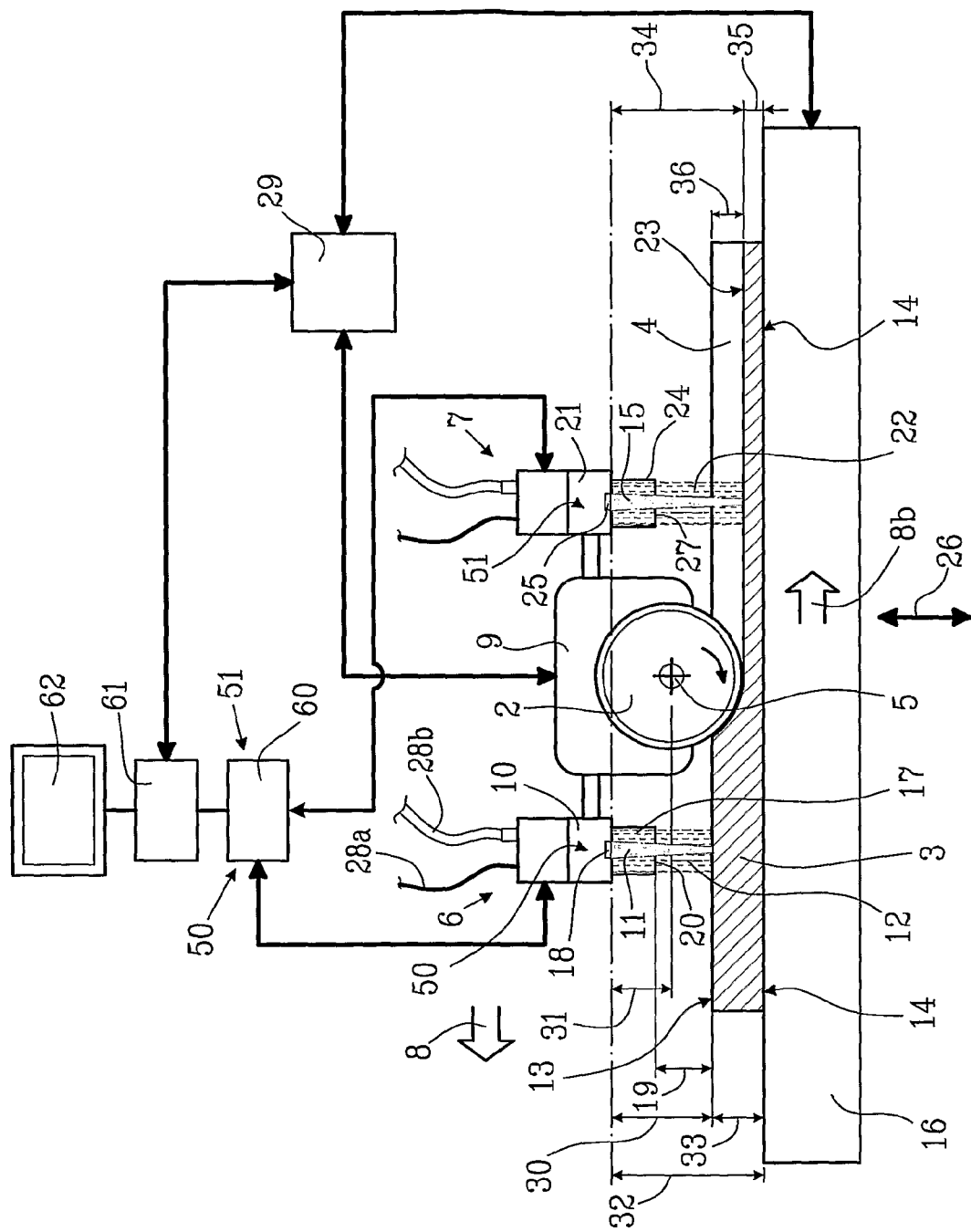
FIG. 1a is a schematic view of a milling machine and a device according to the invention, which device may be used when applying the method according to the invention.
Figure 1B:
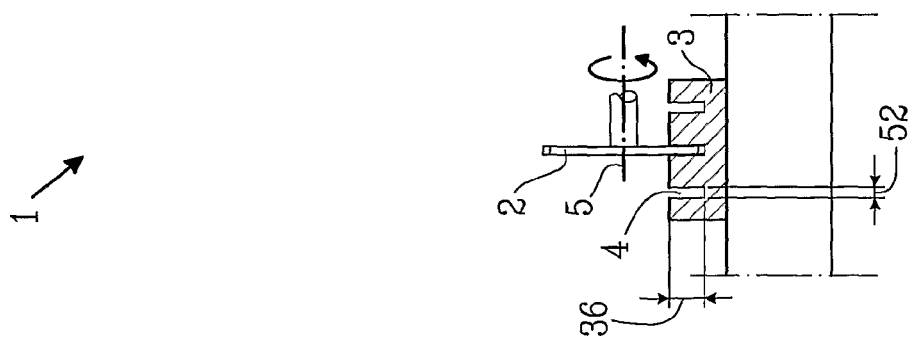
FIG. 1b is a lateral view of the device in FIG. 1.

In FIG. 1a a device 1 for controlling a tool 2 during machining a work piece 3 by means of the tool 2 is illustrated. In the example illustrated in FIG. 1a the tool 2 for machining the work piece 3 is a rotatable side-milling cutter blade arranged to machine grooves 4 in the work piece 3 which in this case is a sheet. The tool 2 is usually provided with hard metal inserts for machining a work piece made of metal. In FIG. 1b the tool 2 and the work piece 3 are illustrated in a lateral view. It should be pointed out that although the rotation axis 5 of the tool 2 is substantially horizontal in FIGS. 1a and 1b, the direction of the rotation axis 5 of the tool 2 is not critical to the invention, and for example a vertical rotation axis may also be used.

In accordance with the invention the device 1 comprises a first measuring arrangement 6, and as appears from FIG. 1a in this particular embodiment of the invention the device 1 also comprises a second measuring arrangement 7. The first measuring arrangement 6 is arranged ahead of the tool 2, or in other words in front of the tool, with respect to the relative tool movement direction 8. The second measuring arrangement 7 is arranged after the tool 2, or in other words behind the tool, with respect to the relative tool movement direction 8. Both the first 6 and the second measuring arrangement 7 are moveable relative to the work piece 3 in the relative tool movement direction 8, preferably together with the tool 2. This movement of the first and second measuring arrangements 6, 7 may be accomplished by attachment of the first and second measuring arrangement to a unit 9 carrying the tool 2. In other words, the relative positions of the carrying unit 9 and the first and second measuring arrangements 6, 7 can be fixed. Thus, a relative movement between the tool 2 and the work piece 3 implies the same relative movement between the first and second measuring arrangements 6, 7 on one hand, and the work piece 3 on the other hand.

By "the relative tool movement direction" 8 is meant the direction in which the tool 2 is moved relative to the work piece 3 during operation. However, this relative movement may be achieved by moving (to the left in FIG. 1a) the unit 9 which carries the tool 2 or by moving the work piece 3 in the opposite direction 8b. Thus, during a milling operation this relative movement between the tool 2 and the work piece 3 is a translation movement. In addition to the translation movement the milling tool 2 is rotated around its rotation axis 5.

Although the invention is illustrated when applied during a milling operation, the invention can be applied in connection with other machining operations, such as turning. When applying the invention during a turning operation, the relative movement and the relative movement direction are then instead determined by the rotation of the work piece relative to the tool.

The first measuring arrangement 6 comprises a first ultrasonic probe 10 for emitting ultrasonic waves 11. The probe functions as a transmitter and a receiver of the waves. The expression "ultrasonic waves" used herein comprises sonic waves having a frequency well above 20 kHz, preferably in the interval 1-100 MHz. In many applications a frequency in the interval 5-30 MHz is used, preferably 25 MHz.

The ultrasonic waves 11 emitted by the first ultrasonic probe 10 are transmitted to the work piece 3 and transmitted back to the first ultrasonic probe 10 by means of a first column of liquid 12. The liquid 12 can be water or any other water solution or other liquid suitable for transmitting ultrasonic waves. The liquid column has a limited cross section area adapted to the ultrasonic beam, and is surrounded by the atmosphere, usually air. This first liquid column 12 can at the same time be used as a cutting fluid for facilitating the machining process and/or cooling the tool 2 and the work piece 3. Furthermore, the probe is provided with means for powering the probe, and means for supplying liquid to the probe. These means are schematically illustrated as an electric cable 28a and a water hose 28b, respectively.

The electric cable can also be used for communication of signals to and from the probe. The first measuring arrangement 6 preferably comprises a first nozzle 17 for forming the first column of liquid 12 as a jet directed to the work piece 3. The liquid jet direction is preferably substantially perpendicular to the current surface of the work piece to be machined. The flow of the jet is preferably substantially a laminar flow.

In FIG. 1a the first ultrasonic probe 10 is integrated with the first nozzle 17. Inside the first ultrasonic probe 10 an emitting unit 18 such as a piezo-electric crystal is arranged to emit the ultrasonic waves. The ultrasonic probe and the nozzle are suitably integrated so as to create the jet 12 extending from the emitting unit 18 of the probe to the work piece 3. The first nozzle 17 can be arranged at a certain distance 19 from the work piece 3 so as to form a space between the outer end 20 of the first nozzle 17 and the work piece 3 where the jet of liquid is able to flow freely. The emitting unit constitutes a combined emitting and receiving unit. However, in another embodiment of the invention both an emitting unit and a separate unit for receiving the reflected ultrasonic waves can be arranged inside the probe.

When reaching a first, upper surface 13 of the work piece 3 some of the ultrasonic waves are reflected back to the probe, i.e. giving a first echo from the first surface 13, whereas some of the ultrasonic waves are transported further through the work piece 3 and when reaching a second, lower surface 14 of the work piece 3 they are reflected back to the probe, i.e. giving a second echo from the second surface 14. In addition, the ultrasonic beam gives multiple echoes from the first and second surfaces 13, 14 before being attenuated. One or more of these multiple signals can be used to improve the accuracy of the measurements.

The second measuring arrangement 7 comprises a second ultrasonic probe 21 for emitting ultrasonic waves 15. The probe functions as transmitter and a receiver of the waves. The ultrasonic waves emitted by the second ultrasonic probe 21 are transmitted to the work piece 3 and transmitted back to the second ultrasonic probe 21 by means of a second column of liquid 22. Furthermore, the probe is provided with means for powering the probe, and means for supplying liquid to the probe. The second measuring arrangement 7 preferably comprises a second nozzle 24 for forming the second column of liquid 22 as a jet directed to the work piece 3. In FIG. 1a the second ultrasonic probe 21 is integrated with the second nozzle 24. Inside the second ultrasonic probe 21 an emitting unit 25 such as a piezo-electric crystal is arranged to emit the ultrasonic waves. The ultrasonic probe and the nozzle are suitably integrated so as to create the jet 22 extending from the emitting unit 25 of the probe to the work piece 3. The second nozzle 24 can be arranged at a certain distance from the work piece 3 so as to form a space between the outer end 27 of the second nozzle 24 and the work piece 3 where the jet 22 of liquid is able to flow freely. The emitting unit constitutes a combined emitting and receiving unit. However, in another embodiment of the invention both an emitting unit and a separate unit for receiving the reflected ultrasonic waves can be arranged inside the probe.

When reaching a machined surface 23 of the work piece 3 some of the ultrasonic waves are reflected back to the probe, i.e. giving a first echo from the machined surface 23, whereas some of the ultrasonic waves are transported further through the work piece 3 and when reaching the second surface 14 of the work piece 3 they are reflected back to the probe, i.e. giving a second echo from the second surface 14. In addition, the ultrasonic beam gives multiple echoes from the machined surface 23 and the second surface 14 before being attenuated. One or more of these multiple signals can be used to improve the accuracy of the measurements.

The device according to the invention comprises a means 50 for providing signals based on the measurements accomplished by the first ultrasonic probe 10. The signals provided are receivable by a control unit 29 for automatically adjusting the position of the tool 2 relative to the work piece during machining the work piece. The signal means 50 can be constituted by the piezo-electric crystal 18, which generates an alternating voltage, or by the piezo-electric crystal 18 together with any further conventional equipment arranged inside and/or outside the probe. A standard ultrasonic probe which is able to transmit and receive ultrasonic waves and produce an electric signal based on the received waves may be used, provided that the probe fulfils other occurring requirements. The signals can be obtained by using such a probe and eventually one or more standard electric components. Examples of such standard components are amplifiers, filters and/or A/D converters, etc. In an embodiment where the second ultrasonic probe 21 is used, this probe is suitably provided with a means 51 designed to provide signals receivable by the control unit 29 in the same way as the first ultrasonic probe 10.

In the embodiment illustrated in FIG. 1a, the device 1 comprises an ultrasonic system 60 which communicates with the first 10 and second 21 probes. From the ultrasonic system 60 the probes are fed with pulses and signals received by the probes are transferred back to the ultrasonic system. The ultrasonic system 60 suitably comprises the above-mentioned components as amplifiers, filters and/or A/D converters for processing the signals. A computer unit 61 provided with a monitor 62 is used to run the ultrasonic system 60 by executing a computer program. The computer unit 61 can also be used for storing and/or displaying the measured distances to the work piece and/or the measured wall thicknesses of the work piece. Furthermore, the computer unit 61 is connected to the control unit 29 of the milling machine so as to provide control signals for adjusting the tool position.

The computer program may comprise an instruction set stored in an internal memory of the computer to instruct a processor for accomplishing the steps of the method when the instruction set is executed in the computer. The computer program can be provided at least partly via a network such as the Internet. The computer may be designed for receiving a computer readable medium having a stored program or data thereon intended to cause the computer to control the steps of the method according to the invention.

The measurements which can be accomplished by the first and second ultrasonic probes can be divided into distance measurements and thickness measurements.

By measuring the propagation time of the first echo, the distance 30 between the first ultrasonic probe 10 and the first surface 13 of the work piece 3 can be calculated. Knowledge about the distance 30 from the first ultrasonic probe 10 to the first surface 13 of the work piece makes it possible to calculate the position of the tool 2 relative to the work piece 3, since the distance 31 from the first ultrasonic probe 10 to the tool is predetermined. By measuring the propagation time of the second echo in the work piece 3, the distance between the first surface 13 and the second surface 14, i.e. the thickness 33 of the work piece 3, can be calculated.

In the same way, the first echo received by the second ultrasonic probe 21 gives information about the distance 34 between the second ultrasonic probe 21 and the machined surface 23 of the work piece 3. Knowledge about the distance 34 from the second ultrasonic probe 21 to the machined surface 23 of the work piece 3, together with information about the original thickness 33 of the work piece or the distance 32 to the second surface 14 makes it possible to calculate the current thickness 35 of the work piece. Using information about the original distance 30 to the first surface 13 and the distance to the machined surface 23 makes it possible to calculate the real cutting depth 36. By measuring the propagation time of the second echo, the distance between the machined surface 23 and the second surface 14, i.e. thickness 35 of the of the work piece, can be calculated.

The control unit 29 receiving signals from the computer unit 61 is in turn able to emit signals to the milling machine to control the movement of the tool carrying unit 9 and/or the sliding carriage 16 supporting the work piece 3. Generally, the relative movement may be achieved by moving the work piece 3 or moving the tool 2. For example, the milling machine can be a so called NC or CNC milling machine. In the embodiment illustrated in FIG. 1a the tool 2 and the work piece 3 can be brought towards each other or away from each other in the vertical direction 26 by controlling a motor (not shown) driving the sliding carriage 16.

According to a first example, the position of the tool 2 relative to the work piece 3 is adjusted based only on the calculated distance from the first ultrasonic probe 10 to the first surface. According to a second example, the position of the tool 2 relative to the work piece 3 is adjusted based only on the calculated thickness 33 of the work piece 3 between the first surface 13 and a second surface 14 of the work piece 3. According to a third example, the position of the tool 2 relative to the work piece 3 is adjusted based on both the calculated distance from the first ultrasonic probe 10 to the first surface and on the calculated thickness 33 of the work piece 3 between the first surface 13 and a second surface 14 of the work piece 3.

According one embodiment of the second example, ie when the position of the tool 2 relative to the work piece 3 is adjusted based only on the calculated thickness 33 of the work piece 3 between the first surface 13 and a second surface 14 of the work piece 3, a serie of steps are performed; a) the tool 2 is brought into contact with the work piece before the machining operation is initiated, b) a wall thickness is calculated at the point of contact, and c) the tool is controlled to a nominal engagement depth based on the calculated wall thickness so that the wall thickness of the meachined portion of the work piece 3 is not less than a tolerance requirement.

In some applications a focused beam of ultrasonic waves is very usable. This is particularly the case when machining narrow grooves and/or machining a work piece having a curved surface. By focusing the beam the ultrasonic waves can be directed into the groove without being disturbed by the surface close to the groove or by the edges of the walls defining the groove. This means the beam can be directed into the groove and substantially the entire cross section of the beam can reach the bottom of the groove so as to measure the wall thickness of the work piece between the machined bottom surface 23 of the groove and the second surface 14. Furthermore, a focused beam concentrates the measurement on a limited and well defined area of the work piece.

When discussing herein the terms focal distance, focal length or depth, and focal diameter, the following definitions have been used; the focal distance is the distance between the emitting unit and the position at the ultrasonic beam where the beam is focused to a focal diameter, the focal length is the extension of the ultrasonic beam having an appropriate focal diameter, and the diameter of the ultrasonic beam is the extension of the beam in a cross section of the ultrasonic beam. Please observe that the focal diameter is normally allowed to vary within a certain interval.

Figure 2A:
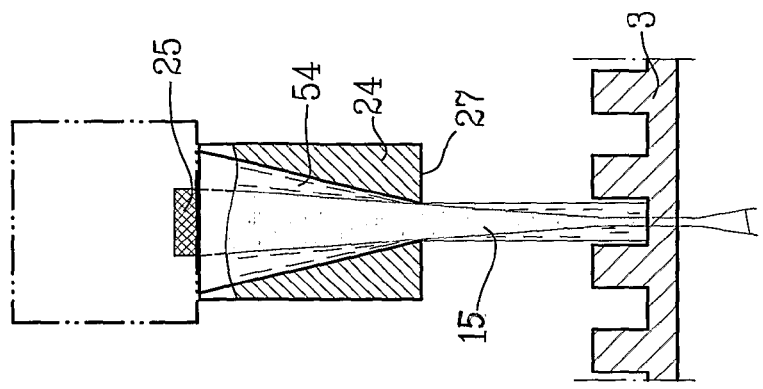
FIG. 2a is a schematic view of an emitting unit of an ultrasonic probe and an ultrasonic beam emitted from the emitting unit, the beam being arranged to propagate in a jet of liquid.

In FIG. 2a a probe with an emitting unit 18, and an ultrasonic beam 11 and a jet of liquid 12 are schematically illustrated. Generally the liquid jet may have an extension 30 from the emitting unit 18 to the work piece 3 in the interval 5-150 mm, and preferably 10-100 mm. Although the illustrated liquid jet 12 has a larger diameter D than the beam 11, the liquid jet diameter D as well as the beam diameter d can be different for other applications, and for example, the liquid jet and the beam could have substantially the same cross section diameter. Both the liquid diameter and the beam diameter are preferably adapted to the shape of the work piece. In the case of a substantially plane surface as illustrated in FIG. 2a the diameters are not so critical, provided that the jet diameter D is at least equal to the beam diameter d such that sufficient echoes of the ultrasonic waves are obtained.

According to the embodiment shown in FIG. 2a, the first ultrasonic probe 10 emits an unfocused beam of ultrasonic waves. Thus, the extension of the beam perpendicular to its longitudinal direction is substantially constant, or somewhat diverging. By emitting an unfocused beam with a beam diameter d according to above, any relatively small irregularities and variations in the surface within the beam diameter d may be detected and the distance to the work piece 3 and/or thickness of the work piece may be calculated accurately irrespective of such irregularities/variations.

Figure 2B:
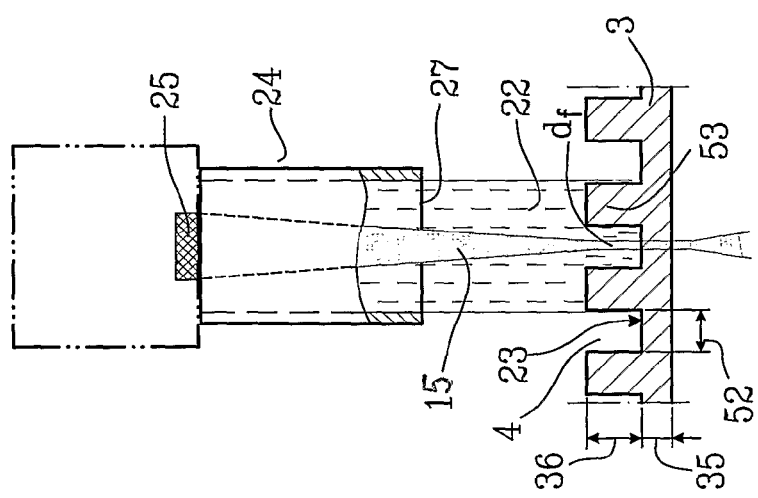
FIG. 2b is a view corresponding to FIG. 2a, wherein the ultrasonic beam is focused.

However, a more complicated geometry of the work piece 3, such as grooves 4 cut into the surface, means that the jet diameter D and/or the beam diameter d have to be adapted to the dimensions of the work piece 3. In FIG. 2b the ultrasonic beam 15 is focused so as to obtain a smaller focal diameter df adapted to the width 52 and the depth 36 of the groove 4. Thereby, the entire cross section of the beam hits the bottom surface 23 of the groove 4. Thus, measurements with respect to the bottom surface can be accomplished. Although dependent on the geometry of the work piece 3, the focal diameter df is often in the interval 0.1-2 mm, preferably 0.3-1.5 mm, and more preferably 0.4-1 mm. The focal point is situated ahead of the outlet 27 of the nozzle 24, and preferably the focal point is situated 1-10 mm ahead of the outlet 27 of the nozzle 24.

The jet diameter D is preferably at least 2 times the width 52 of the current groove 4. Preferably, the jet is centred relative to the groove 4. In this way by using a relatively large jet diameter D the laminar flow of the jet is not much disturbed by the surrounding portions of the work piece 3. A laminar flow and a minimum of disturbances of the flow when hitting the surface promote a favourable propagation of the ultrasonic waves. Such a liquid jet 22 has often a diameter close to the work piece in the interval 5 to 20 mm. In this example, the diameter D corresponds substantially to the extension of the width of one groove 4 and two ridges 53 situated adjacent to the groove.

Figure 2C:
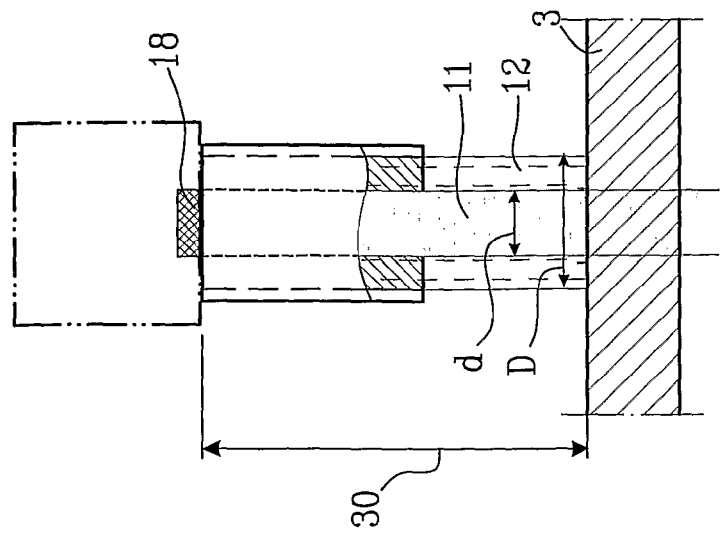
FIG. 2c is a view corresponding to FIG. 2b, wherein the jet of liquid is converged.

In FIG. 2c the liquid jet is convergent. The nozzle 24 has a conical channel 54 for forming the jet of liquid. This means the jet of liquid is convergent inside the nozzle 24 in the direction from the emitting unit 25 towards the mouth 27 of the nozzle. By such a nozzle the jet can be adapted to the shape of the work piece. For example, the size of the jet diameter can be adapted to the size of a groove into which the jet is directed. This can counteract disturbance of the jet. Although dependent on the geometry of the work piece, the cross section diameter of the jet close to the work piece is often in the interval 0.2 to 1 mm when using a convergent ultrasonic beam.

It is to be understood that the present invention is not limited to the embodiments described above and illustrated in the drawings; rather, the skilled person will recognize that many changes and modifications may be made within the scope of the appended claims.

According to an alternative to the embodiment shown in FIG. 2b, the first ultrasonic probe 10 emits a focused beam of ultrasonic waves. The beam diameter of such a focused beam is preferably controlled to a value corresponding to, ie the same as or close to, the width of the machining tool. In this way, an accurate measurement of exactly the work piece area to be machined by the tool may be measured. Thus, the distance to the work piece 3 and/or thickness of the work piece may be calculated accurately.

The invention claimed is:

1. A method for controlling a tool during machining a work piece with the tool, comprising
    using a first measuring arrangement having a first ultrasonic probe for emitting ultrasonic waves, the first measuring arrangement being arranged ahead of the tool with respect to a relative tool movement direction and being moved relative to the work piece in the relative tool movement direction,
    transmitting ultrasonic waves emitted by the first ultrasonic probe to the work piece, and transmitting the ultrasonic waves that have been transmitted to the work piece back to the first ultrasonic probe using a first column of liquid which is created by the first measuring arrangement and is situated between the first ultrasonic probe and the work piece for measurement,
    using a measurement obtained by the first measuring arrangement for automatically adjusting a position of the tool relative to the work piece during machining the work piece,
    using a second measuring, arrangement having a second ultrasonic probe for emitting ultrasonic waves, the second measuring arrangement being arranged after the tool with respect to the relative tool movement direction and being moved relative to the work piece in the relative tool movement direction,
    transmitting ultrasonic waves emitted by the second ultrasonic probe to a machined surface of the work piece that has been machined by the tool and back to the second ultrasonic probe by means of a second column of liquid which is created by the second measuring arrangement and is situated between the second ultrasonic probe and the machined surface, and
    using the measurements obtained by the second ultrasonic probe for automatically adjusting the position of the tool relative to the work piece during machining the work piece.

2. A method according to claim 1, comprising transmitting the ultrasonic waves emitted by the first ultrasonic probe to a first surface of the work piece, wherein the first column of liquid is situated between the first ultrasonic probe and the first surface, for measuring a distance from the first ultrasonic probe to the first surface, and using distance measurements for automatically adjusting the position of the tool relative to the work piece during machining the work piece.

3. A method according to claim 1, wherein using the first ultrasonic probe for measuring a thickness of the work piece between the first surface and a second surface of the work piece, and using thickness measurements for automatically adjusting the position of the tool relative to the work piece during machining the work piece.

4. A method according to claim 1, comprising using the second ultrasonic probe for measuring thickness of the work piece between the machined surface and the second surface.

5. A method according to claim 1, comprising using the second ultrasonic probe for measuring distance from the second ultrasonic probe to the machined surface and calculating the thickness of the work piece between the machined surface and the second surface by means of the measured distance.

6. A method according to claim 4, comprising recording the thickness between the machined surface and the second surface of the work piece.

7. A method according to claim 1, comprising using a first nozzle for forming the first column of liquid in a form of a jet directed to the work piece.

8. A method according to claim 7, wherein arranging the first nozzle at a certain distance from the work piece so as to form a space between the first nozzle and the work piece where the jet of liquid is able to flow freely.

9. A method according to claim 1, comprising using the first ultrasonic probe for emitting an unfocused beam of ultrasonic waves.

10. A method according to claim 1, comprising using a second, nozzle for forming the second column of liquid in a form of a jet directed to the work piece.

11. A method according to claim 10, comprising arranging the second nozzle at a certain distance from the work piece so as to form a space between the second nozzle and the work piece where the jet of liquid is able to flow freely.

12. A method according to claim 10, wherein the second nozzle has an internal conical channel for forming the jet of liquid, the jet of liquid being convergent inside the second nozzle.

13. A method according to claim 7, comprising creating a substantially laminar flow of the jet of liquid.

14. A method according to claim 1, comprising using the second ultrasonic probe for emitting a focused beam of ultrasonic waves.

15. A method according to claim 10, comprising using the second ultrasonic probe for emitting a focused beam of ultrasonic waves, the beam having a focal point situated ahead of an outlet of the second nozzle.

16. A method according to claim 15, wherein the beam has a focal point situated 1-10 mm ahead of the outlet of the second nozzle.

17. A method according to claim 15, wherein the focused beam of ultrasonic waves has a focal diameter in the interval 0.1-2 mm.

18. A method according to claim 15, wherein the focused beam of ultrasonic waves has a focal length of at least 1 mm.

19. A method according to claim 1, wherein the second column of liquid has an extension from an emitting unit of the second ultrasonic probe to the work piece of 5-150 mm.

20. A method according to claim 1, wherein the second column of liquid has a cross section diameter proximate the work piece of 0.2-20 mm.

21. A method according to claim 1, comprising, using the method for machining a groove in the work piece.

22. A method according to claim 21, comprising using a second measuring arrangement having a second ultrasonic probe for emitting ultrasonic waves, the second measuring arrangement being arranged after the tool with respect to the relative tool movement direction and being moved relative to the work piece in the relative tool movement direction, wherein ultrasonic waves emitted by the second ultrasonic probe are transmitted to a machined surface of the work piece that has been machined by the tool and are transmitted back to the second ultrasonic probe by means of a second column of liquid which is created by the second measuring arrangement and is situated between the second ultrasonic probe and the machined surface, and using the measurements accomplished by the second ultrasonic probe for automatically adjusting the position of the tool relative to the work piece during machining the work piece, and arranging the second column of liquid centered relative to the current groove.

23. A method according to claim 21, comprising using a second measuring arrangement having a second ultrasonic probe for emitting ultrasonic waves, the second measuring arrangement being arranged after the tool with respect to the relative tool movement direction and being moved relative to the work piece in the relative tool movement direction, wherein ultrasonic waves emitted, by the second ultrasonic probe are transmitted to a machined surface of the work piece that has been machined by the tool and are transmitted back to the second ultrasonic probe by means of a second column of liquid which is created by the second measuring arrangement and is situated between the second ultrasonic probe and the machined surface, and using the measurements accomplished by the second ultrasonic, probe for automatically adjusting the position of the tool relative to the work piece during machining the work piece, and wherein the second column of liquid has a cross section diameter which, proximate the work piece, is smaller than a width of the groove.

24. A method according to claim 21, comprising using a second measuring arrangement having a second ultrasonic probe for emitting ultrasonic waves, the second measuring arrangement being; arranged after the tool with respect to the relative tool movement direction and being moved relative to the work piece in the relative tool movement direction, wherein ultrasonic waves emitted by the second ultrasonic probe are transmitted to a machined surface of the work piece that has been machined by the tool and are transmitted back to the second ultrasonic probe by means of a second column of liquid which is created by the second measuring arrangement and is situated between the second ultrasonic probe and the machined surface, and using the measurements accomplished by the second ultrasonic probe for automatically adjusting the position of the tool relative to the work piece during machining the work piece, and wherein the second column of liquid has a cross section diameter which, proximate the work piece, is at least 2 times the width of the groove.

25. A method according to claim 1, wherein the second ultrasonic probe emits a beam of ultrasonic waves, the beam having a cross section diameter, close to a bottom of the groove, which diameter is smaller than the width of the groove.

26. A non-transient storage medium comprising a computer program for instructing a processor to accomplish the steps according to claim 1 when the program is run in a computer.

27. A device for controlling a tool during machining a work piece with the tool, comprising:
a first measuring arrangement having a first ultrasonic probe for emitting ultrasonic waves, the first measuring arrangement being adapted to be arranged ahead of the tool with respect to a relative tool movement direction and to be moved in the relative tool movement direction, the first measuring arrangement having, a first nozzle for creating a first column of liquid between the first ultrasonic probe and the work piece for transmitting ultrasonic waves from the first ultrasonic probe to the work piece and reflected ultrasonic waves from the work piece to the first ultrasonic probe, and means for providing signals based on the measurements accomplished by the first ultrasonic probe which signals are receivable by a control unit for automatically adjusting a position of the tool relative to the work piece during machining the work piece, and a second measuring arrangement having a second ultrasonic probe for emitting ultrasonic waves, the second measuring arrangement being adapted to be arranged after the tool with respect to the relative tool movement direction and to be moved in the relative tool movement direction, the second measuring arrangement having a second nozzle for creating a second column of liquid between the second ultrasonic probe and a machined surface of the work piece machined by the tool for transmitting ultrasonic waves from the second ultrasonic probe to the machined surface and reflected ultrasonic waves from the work piece to the second ultrasonic probe, and means for signals based on the measurements accomplished by the second ultrasonic probe which signals are receivable by a control unit for automatically adjusting the tool relative to the work piece during machining the work piece.

28. A milling machine comprising a device for controlling a tool during machining a work piece with the tool, the device comprising:
a first measuring arrangement having a first ultrasonic probe for emitting ultrasonic waves, the first measuring arrangement being adapted to be arranged ahead of the tool with respect to a relative tool movement direction and to be moved in the relative tool movement direction, the first measuring arrangement having a first nozzle for creating a first column of liquid between the first ultrasonic probe and the work piece for transmitting ultrasonic waves from the first ultrasonic probe to the work piece and reflected ultrasonic waves from the work piece to the first ultrasonic probe, and means for providing signals based on the measurements accomplished by the first ultrasonic probe which signals are receivable by a control unit for automatically adjusting a position of the tool relative to the work piece during machining the work piece, and a second measuring arrangement having a second ultrasonic probe for emitting ultrasonic waves, the second measuring arrangement being adapted to be arranged after the tool with respect to the relative tool movement direction and to be moved in the relative tool movement direction the second measuring arrangement having a second nozzle for creating a second column of liquid between the second ultrasonic probe and a machined surface of the work piece machined by the tool for transmitting ultrasonic waves from the second ultrasonic probe to the machined surface and reflected ultrasonic waves from the work piece to the second ultrasonic probe, and means for providing signals based on the measurements accomplished by the second ultrasonic probe which signals are receivable by a control unit for automatically adjusting the tool relative to the work piece during machining the work piece.

* * * * *